US00PP37008P2

(12) United States Plant Patent
Nishikawa

(10) Patent No.: US PP37,008 P2
(45) Date of Patent: Oct. 7, 2025

(54) ***DELOSPERMA* PLANT NAMED 'T2160'**

(50) Latin Name: *Delosperma nubigenum*
Varietal Denomination: T2160

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 19/189,144

(22) Filed: Apr. 24, 2025

(30) Foreign Application Priority Data

Nov. 21, 2024 (QZ) ..... PBR 20242720

(51) Int. Cl.
*A01H 6/30* (2018.01)
*A01H 5/02* (2018.01)

(52) U.S. Cl.
USPC ..... Plt./422

(58) Field of Classification Search
USPC ..... Plt./422
CPC ..... A01H 6/30; A01H 5/02
See application file for complete search history.

*Primary Examiner* — Keith O. Robinson
(74) *Attorney, Agent, or Firm* — Penny J. Aguirre

(57) ABSTRACT

A new cultivar of *Delosperma* plant named 'T2160' that is characterized by its very large flowers, its very floriferous and long blooming flowering habit; blooming from early summer to early autumn, its flowers with coloration that is red-orange with light orange centers and flushed with fuchsia, its low-growing plant habit, and its high petal count.

3 Drawing Sheets

Botanical classification: *Delosperma nubigenum.*
Variety denomination: 'T2160'.

CROSS-REFERENCE TO RELATED APPLICATIONS

This application claims priority to European Community Plant Variety Office (CPVO) Plant Breeder's Rights Application No. 2024/2720 filed on Nov. 21, 2024, under 35 U.S.C. 119(f), the entire contents of which is incorporated by reference herein.

BACKGROUND OF THE INVENTION

The present invention relates to a new and distinct cultivar of *Delosperma* plant, botanically known as *Delosperma nubigenum* 'T2160' and will be referred to hereinafter by its cultivar name, 'T2160'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with compact plant habits, floriferous blooming habits, and large flowers in a unique range of flower colors.

'T2160' was selected in the Inventor's trial garden in May of 2018 as a single unique plant from amongst the seedlings derived from a cross between unnamed and unpatented plants from the Inventor's breeding program.

Asexual propagation of the new cultivar was first accomplished by stem cuttings in September of 2018 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar.

These attributes in combination distinguish 'T2160' as a unique cultivar of *Delosperma.*

1. 'T2160' exhibits very large flowers.
2. 'T2160' exhibits a very floriferous and long blooming flowering habit; blooming from early summer to early autumn.
3. 'T2160' exhibits flowers with coloration that is red-orange with light orange centers and flushed with fuchsia.
4. 'T2160' exhibits a low-growing plant habit.
5. 'T2160' exhibits a high petal count.

Both the female and male parents are similar to 'T2160' in having flowers with orange coloration. The female parent differs from 'T2160' in having a more vigorous growth habit. The male parent differs from 'T2160' in having a more compact plant habit. 'T2160' can be most closely compared to the *Delosperma* cultivars 'T1873' (U.S. Plant Pat. No. 34,674) and 'W1813' (U.S. Plant Pat. No. 34,533). 'T1873' is similar to 'T2160' in having a low growing plant habit, a high flower count, and large flowers. 'T1873' differs from 'T2160' in having flowers that are orange in color with magenta tips and yellow centers. 'W1813' is similar to 'T2160' in having a low-growing plant habit and a high flower count. 'W1813' differs from 'T2160' in having flowers that are much smaller in size and bright orange-red in color with small yellow centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include a website listing by Florensis.

BRIEF DESCRIPTION OF THE DRAWINGS

The accompanying color photographs illustrate the overall appearance and distinct characteristics of the new *Delosperma*. The photographs were taken of a plant about 1 year in age (from a plug) as grown in an unheated greenhouse in Waddinxveen, Netherlands.

The photograph in FIG. 1 provides a side view of 'T2160' in bloom.

Figure 1:
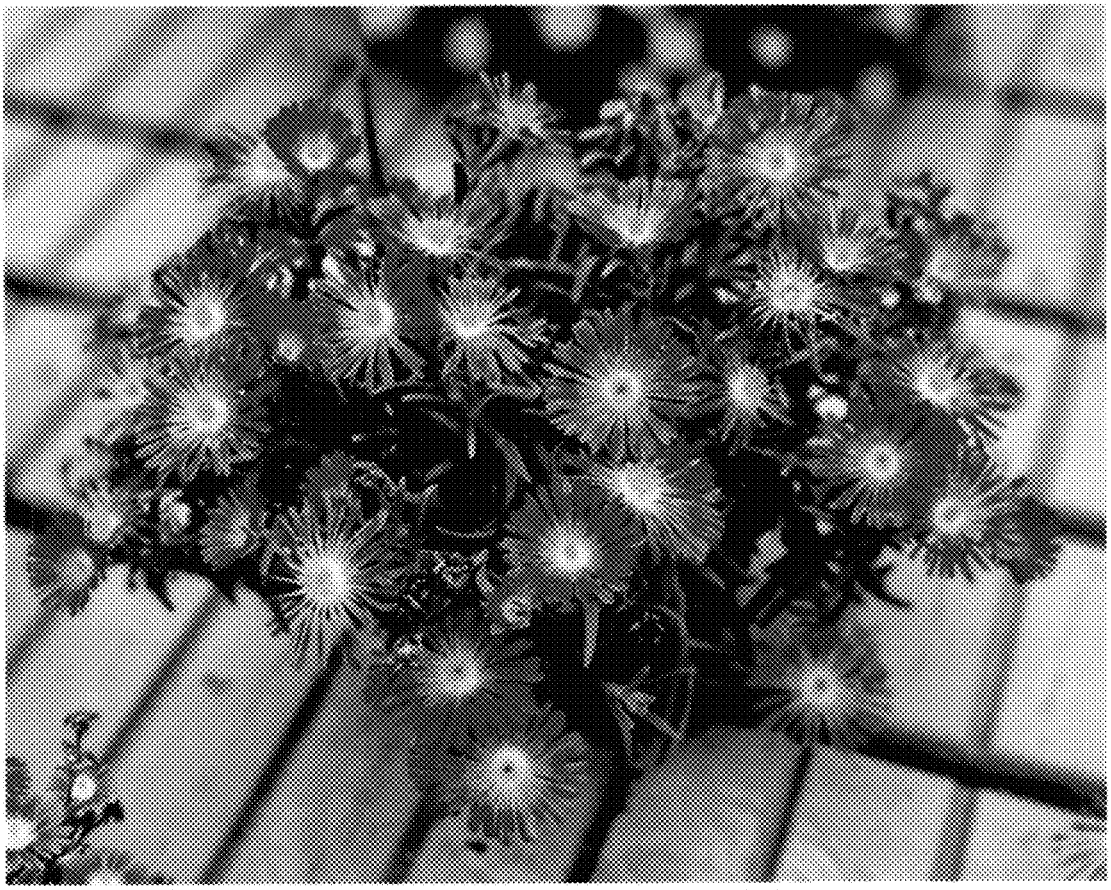
Figure 2:
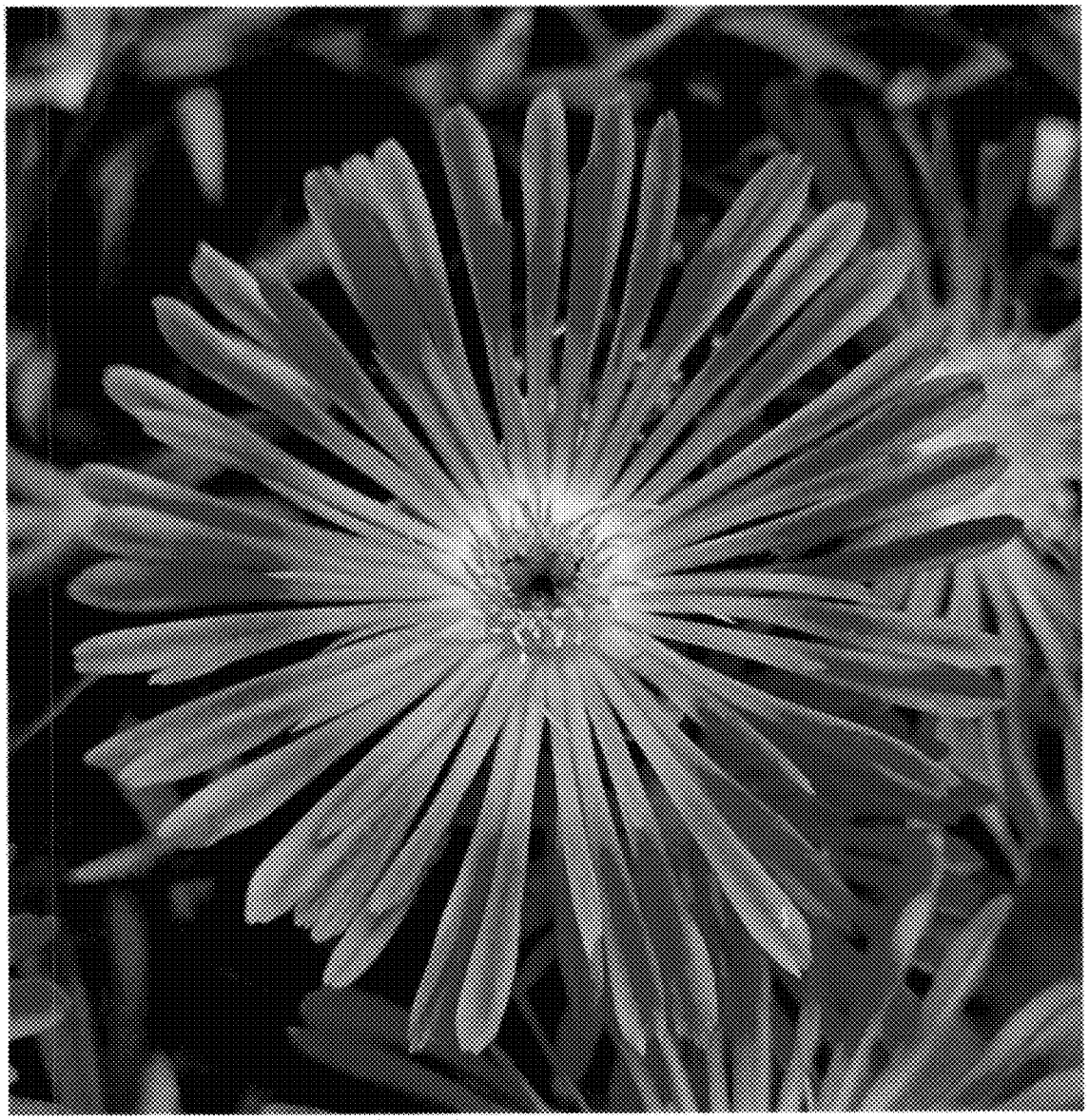

The photograph in FIG. 2 provides a view of a flower of 'T2160'.

Figure 3:
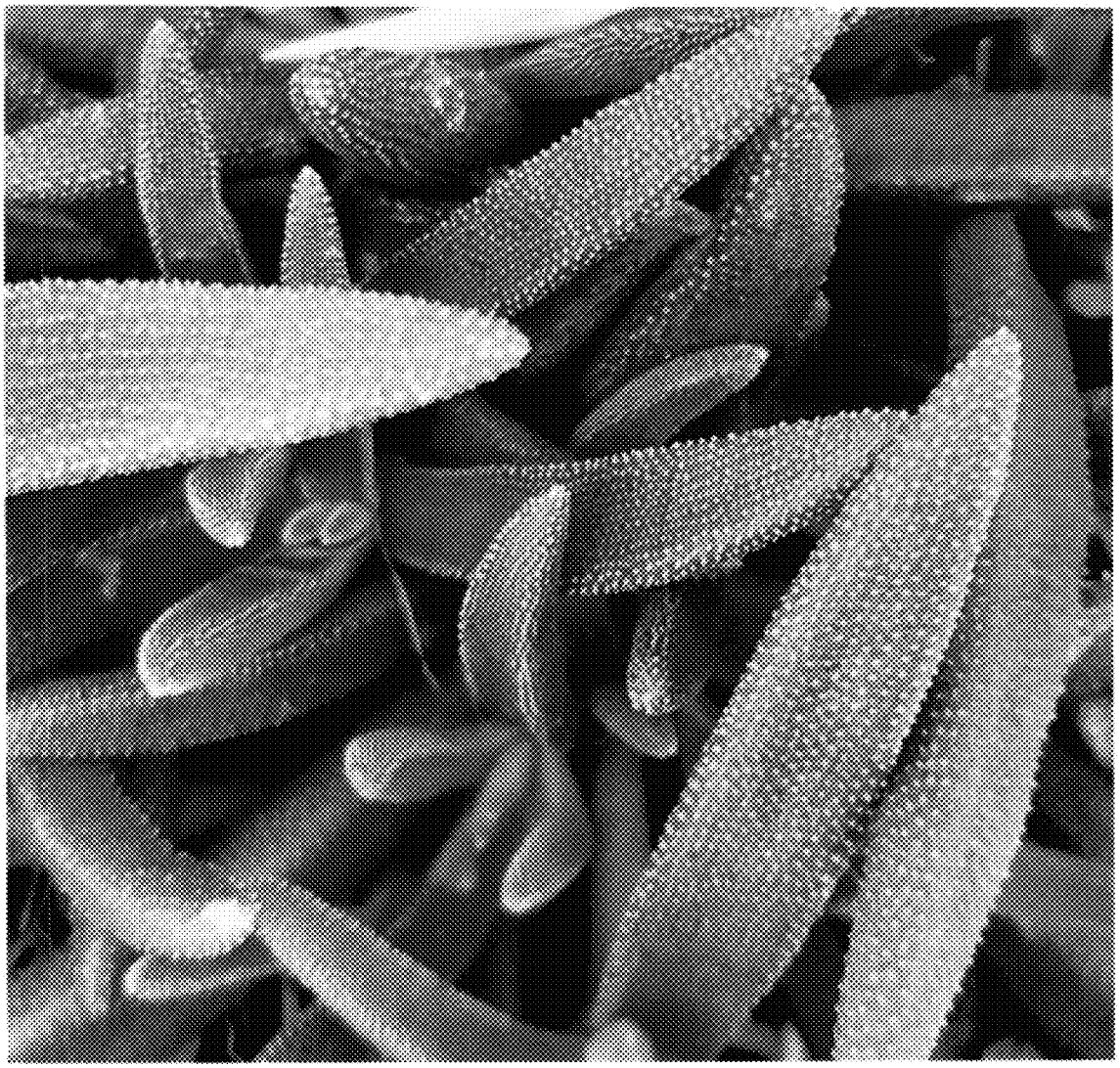

The photograph in FIG. 3 provides a close-up view of the foliage of 'T2160'.

The colors in the photographs may differ slightly from the color values cited in the detailed botanical description, which accurately describe the colors of the new *Delosperma*.

DETAILED BOTANICAL DESCRIPTION

The following is a detailed description of 3.5-month-old plants of the new cultivar as grown in 15-cm containers in an unheated greenhouse in Waddinxveen, Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early summer to early autumn in The Netherlands.

*Plant type*.—Evergreen perennial.

*Plant habit*.—Flattened, prostrate.

*Height and spread*.—Reaches an average of 8 cm in height and about 17 cm in width as a 3-month-old plant as grown in a container, reaches 10 cm in height and 34 to 40 cm in width as grown in the landscape.

*Cold hardiness*.—Observed to be hardy to at least U.S.D.A. Zone 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a plug to young plant in a P9 container.

*Growth habit*.—Moderate.

Stem description:

*Shape*.—Round.

*Stem color*.—144B to 144C and 183A.

*Stem size*.—Lateral branches; an average of 9 cm in length and 3 mm in diameter.

*Internode length*.—An average of 2 cm.

*Stem substance*.—Succulent.

*Stem surface*.—Moderately glossy, moderately pubescent.

*Branching habit*.—Freely branching both basal and lateral, an average of 14 lateral branches per stem.

Foliage description:

*Leaf shape*.—Ligulate, triangular in diameter.

*Leaf substance*.—Succulent.

*Leaf division*.—Simple.

*Leaf base*.—Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, sparsely to moderately pubescent.

*Leaf color*.—137A, base 145B.

*Leaf size*.—5 cm in length and 7 mm in width.

*Leaf quantity*.—Average of 4 per lateral branch.

*Leaf attachment*.—Sessile.

Inflorescence description:

*Inflorescence type*.—Flowers solitary, terminal.

*Flower number*.—An average of 2 per lateral stem.

*Flower fragrance*.—None.

*Flower aspect*.—Outward to upright.

*Flower longevity*.—Average of 4 days self-cleaning.

*Flower type*.—Single.

*Flower size*.—Average of 4.7 cm in diameter and 1.5 cm in depth.

*Flower buds*.—Broadly ovate to oblong in shape, an average of 1 cm in length and 5 mm in diameter, 42A in color, surface texture is smooth and glossy with the sepal portion smooth and dull.

*Calyx*.—Rotate in shape, average of 9 mm in depth and 2.5 cm in diameter.

*Sepals*.—5, rotate, ovate in shape, margin entire, an average of 1 cm in length and 5 mm in width, broadly acute apex, broadly cuneate base, surface is smooth and dull, color upper and lower surface 137B and 145A.

*Petals*.—An average of 60 to 70 per flower, rotate, oblanceolate in shape, surface is smooth and glossy on both surfaces, margin entire, apex obtuse, base cuneate, an average of 2 cm in length and 3 mm in width, color when opening and fully open upper surface; base NN155A, towards center and tip 23B with 25B, 34A and a stripe of NN78A, color when open and fully open lower surface; NN78A, 75B and N155A, margins 33A.

*Petaloids*.—An average of 20 per flower, rotate and near vertical surrounding stamens, lanceolate in shape, glossy on both surfaces, entire margins, apex obtuse, base truncate, an average of 1 cm in length and 1 mm in width, color upper and lower surface; 23B to 23C.

*Peduncle*.—Average of 2.5 cm in length and 3 mm in diameter, straight on top of lateral branch at 0°, 145A in color, surface moderately glossy, sparsely to moderately pubescent.

*Pedicel*.—None.

Reproductive organs:

*Pistils*.—5, an average of 2 mm in length, stigma; triangular shaped, style and stigma; (not distinguishable) combined an average of 2 mm in length and 151A in color, ovary; 143C in color.

*Stamens*.—Average of 60, 12A in color, anthers; dorsifixed and narrowly oblong in shape, an average of 0.5 mm in diameter, filaments; 4 mm in length, NN155A in color, anthers; NN155D in color, pollen; moderate to high in quantity and 6A in color.

*Fruit*.—Fruit and seed production was not observed under the conditions tested.

It is claimed:

1. A new and distinct variety of *Delosperma* plant named 'T2160' as described and illustrated herein.

* * * * *